United States Patent [19]

Duvert

[11] Patent Number: 5,866,582
[45] Date of Patent: *Feb. 2, 1999

[54] FUNGICIDAL COMBINATION OF A DICARBOXIMIDE COMPOUND AND CYPRODINIL

[75] Inventor: Patrice Duvert, Lyon, France

[73] Assignee: Rhone-Poulenc Agrochimie, Lyon Cedex, France

[*] Notice: This patent issued on a continued prosecution application filed under 37 CFR 1.53(d), and is subject to the twenty year patent term provisions of 35 U.S.C. 154(a)(2).

[21] Appl. No.: 802,591

[22] Filed: Feb. 19, 1997

Related U.S. Application Data

[63] Continuation of Ser. No. 584,391, Jan. 11, 1996, abandoned.

[30] Foreign Application Priority Data

Jan. 9, 1995 [FR] France ................................. 95 00331

[51] Int. Cl.⁶ .......................... A01N 43/38; A01N 43/50; A01N 43/54; A01N 43/76
[52] U.S. Cl. ......................... 514/275; 514/376; 514/391; 514/421
[58] Field of Search .................. 514/275, 391, 514/376, 421

[56] References Cited

U.S. PATENT DOCUMENTS

| | | | |
|---|---|---|---|
| 4,931,560 | 6/1990 | Hubele | 544/315 |
| 4,997,941 | 3/1991 | Hubele | 544/332 |
| 5,153,200 | 10/1992 | Hubele | 514/275 |

FOREIGN PATENT DOCUMENTS

| | | |
|---|---|---|
| 0310550 | 4/1989 | European Pat. Off. . |
| 2516350 | 5/1983 | France . |
| 151404 | 10/1981 | Germany . |
| 2110934 | 6/1983 | United Kingdom . |
| 2267644 | 12/1993 | United Kingdom . |

OTHER PUBLICATIONS

*Chemical Abstracts*, vol. 119, No. 11, abstract No. 111281, Sep. 13, 1993 (abstract of JP 05 112 408).

English translation of JP 05 112 408, published May 7, 1993.

*Chemical Abstracts*, vol. 119, No. 5, abstract No. 43336, Aug. 2, 1993 (abstract of JP 05 065 205).

English translation of JP 05 065 205, published Mar. 19, 1993.

*The Pesticide Manual*, ninth edition, ed. Charles R. Worthing, The British Crop Protection Council, Surry, England 1991, pp. 501, 859–860 and 703.

*Primary Examiner*—Allen J. Robinson
*Attorney, Agent, or Firm*—Burns, Doane, Swecker & Mathis, L.L.P.

[57] ABSTRACT

Fungicidal combination comprising a compound A which is iprodione, vinclozoline or procymidone, and a compound B which is cyprodinil, also known as 2-phenylamino-4-cyclopropyl-6-methylpyrimidine, fungicidal compositions comprising same, and method of preventing fungal attacks on crops.

16 Claims, No Drawings

FUNGICIDAL COMBINATION OF A DICARBOXIMIDE COMPOUND AND CYPRODINIL

CROSS REFERENCE TO RELATED APPLICATION

This is a continuation of prior U.S. patent application Ser. No. 08/584,391, filed Jan. 11, 1996, now abandoned.

The present invention relates to a fungicidal combination or composition, useful in particular in horticulture and in viticulture, which is based on a dicarboximide compound. The invention also relates to a fungicidal treatment process having the same aim.

Dicarboximide derivatives, such as iprodione, are known which are useful in the treatment of fungal attacks due to grey rot in crops, caused by the phytopathogenic fungus *Botrytis cinerea*.

However, the effectiveness of these compounds is no longer entirely satisfactory, in particular on account of the appearance of fungal strains which are resistant to these compounds.

It in, moreover, always desirable to reduce the doses of chemical products dispersed into the environment in order to combat fungal attack on crops, in particular by reducing the application doses of the products, and to widen the possible choices offered to the grower, in order for him to be able to find the solution which is best suited to his particular problem.

One aim of the invention is thus to provide a novel fungicidal combination or composition which is useful for the problems outlined above.

Another aim of the invention is to propose a novel fungicidal combination or composition which in useful in the preventive treatment of grey rot in crops.

It has now been found that these aims could be fully or partially achieved by means of the fungicidal combination or composition according to the present invention, which makes it possible to observe noteworthy synergistic effects.

The fungicidal combination according to the invention comprises a fungicidally effective amount of a compound A which is iprodione, vinclozoline or procymidone, and a compound B which is cyprodinil, also known as 2-phenylamino-4-cyclopropyl-6-methylpyrimidine.

The fungicidal composition of the invention comprises a fungicidally effective amount of a combination of compound A which is iprodione, vinclozoline or procymidone, and a compound B which is cyprodinil; and a agriculturally acceptable vehicle and/or an agriculturally acceptable surfactant.

Preferably, the fungicidally effective amount of compound A and compound B in the combinations and compositions of the invention is a synergistic fungicidally effective amount.

Iprodione, vinclozoline and procymidone are described in the work: "The Pesticide Manual" 9th edition, by Charles R. Worthing and Raymond J. Hance, published by the British Crop Protection Council.

Cyprodinil is described in European patent publication EP 0310550.

The instant combination or composition is effective, for example, for the treatment of grey rot (*Botrytis cinerea*) in grape vines and in market garden crops such as leguminous crops (in particular lettuce, tomato and Cucurbitaceae), strawberries, peas and floral crops.

The compound A/compound B weight ratio in the combination or composition according to the invention is generally between about 0.5 and about 5, preferably between about 1 and about 3.

According to a preferred variant of the invention, the compound A is 3-(3,5-dichlorophenyl)-N-isopropyl-2,4-dioxoimidazolidine-1-carboxamide, also known as iprodione.

The combinations or compositions according to the invention are also advantageous in terms of the spectrum of activity and the low doses of active materials which can be used, the latter quality being particularly important for readily appreciable ecological reasons.

The fungicidal composition according to the invention usually contains from about 0.5 to about 95% of a mixture of compound A and compound B.

Such a composition may be a concentrated composition, that is to say, the commercial product combining the two active materials. It may also be the diluted composition ready for spraying onto the crop to be treated. In the latter case, the dilution with water may be carried out either using a commercial concentrated composition containing the two active materials (this mixture is known as a "ready-to-use" or "ready mix" mixture), or using the mixture which is made up at the time of use (known as the "tank mix") of two commercial concentrated compositions each containing an active material.

The composition according to the invention may also contain all the usual additives or adjuvants of plant protection compositions, in particular vehicles, surfactants, adhesion agents and flow agents.

In the present account, the term "vehicle" denotes an organic or inorganic, natural or synthetic material with which the active materials are associated in order to facilitate their application onto the plant. This vehicle is thus generally inert and it should be agriculturally acceptable, in particular on the plant treated. The vehicle may be solid (clays, natural or synthetic silicates, silica, resins, waxes, solid fertilizers, etc.) or liquid (water, alcohols, ketones, petroleum fractions, aromatic or paraffinic hydrocarbons, chlorinated hydrocarbons, liquefied gases, etc.).

The surfactant may be an emulsifying, dispersing or wetting agent of ionic or nonionic type. Mention may be made, for example, of polyacrylic acid salts, lignosulfonic acid salts, phenolsulfonic acid salts or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyltaurates), and polyoxyethylated phosphoric esters of alcohols or of phenols. The presence of at least one surfactant is desirable in order to promote the dispersion of the active materials in water and their correct application to the plants.

This composition may also contain all sorts of other ingredients such as, for example, protective colloids, adhesives, thickeners, thixotropic agents, penetration agents, stabilizers, sequestering agents, pigments, dyes and polymers.

More generally, the composition according to the invention may include all the solid or liquid additives corresponding to the usual techniques employed in the formulation of plant protection products.

The composition according to the invention may be in solid, gelled or liquid form and, for liquid compositions, in the form of solutions or suspensions or emulsions or emulsifiable concentrates. Liquid compositions are preferred, both on account of their convenience of use and their simplicity of manufacture.

Solid composition forms which may be mentioned are powders for dusting or dispersion (having an active compounds content which may range up to 100%), wettable powders, and granules for dry-spreading, as well an dispersable or soluble granules.

The wettable powders (or powders to be sprayed), like the dispersable granules, usually contain from about 20 to about 95% of active materials, and, in addition to the solid vehicle, from 0 to about 5% of a wetting agent, from about 3 to about 10% of a dispersing agent and, when necessary, from 0 to about 10% of one or more stabilizers and/or other additives, such as pigments, dyes, penetration agents, adhesives, anti-caking agents, etc. It is clearly understood that some of these compositions, such as the wettable powders or the dispersable granules, are intended to make up liquid compositions at the time of application.

Liquid composition forms which may be mentioned are solutions, in particular water-soluble concentrates, emulsifiable concentrates, emulsions, concentrated suspensions, aerosols and pastes.

The emulsifiable or soluble concentrates usually comprise from about 10 to about 80% of active materials, the ready-to-apply emulsions or solutions themselves containing from about 0.01 to about 20% of active materials. In addition to the solvent, the emulsifiable concentrates may contain, when necessary, from about 2 to about 20% of suitable additives such as the above-mentioned stabilizers, surfactants, penetration agents, corrosion inhibitors, dyes or adhesives. Using these concentrates, emulsions of any desired concentration may be obtained by dilution with water, this being particularly suitable for application to the aerial parts of the plant to be treated. As has already been mentioned, the aqueous dispersions and emulsions, for example the compositions obtained by diluting a wettable powder or an emulsifiable concentrate according to the invention with water, are included in the general scope of the present invention. The emulsions may be of the water-in-oil or oil-in-water type and they may have a thick consistency such as that of a "mayonnaise".

The concentrated suspensions, which may also be applied by spraying, are a stable, fluid product which does not give rise to thickening or to formation of a sediment after storage, and they usually contain from about 10 to about 75% of active materials, from about 0.5 to about 15% of surfactants, from about 0.1 to about 10% of thixotropic agents, from 0 to about 10% of suitable additives, such as pigments, dyes, antifoaming agents, corrosion inhibitors, stabilizers, penetration agents and adhesives, and, as a vehicle, water or an organic liquid in which the active materials are insoluble or only sparingly soluble: certain solid organic materials or inorganic salts may be dissolved in the vehicle in order to help prevent sedimentation or as antifreezes for the water.

The composition according to the invention is prepared according to processes which are known per se.

Thus, in order to obtain the powders to be sprayed or wettable powders, the active materials are intimately mixed with the additional substances in suitable mixers and are ground in mills or other grinders. Powders to be sprayed are thereby obtained, the wettability and placing in suspension of which are advantageous; they may be placed in suspension with water at any desired concentration and these suspensions may be used very advantageously in particular for application to the aerial parts of plants.

In place of the wettable powders, concentrated suspensions or pastes may be made. The conditions and embodiments and modes of use of these pastes are similar to those of the wettable powders or powders to be sprayed, part of the necessary grinding operation simply being performed in a liquid medium.

The dispersable granules are usually prepared by agglomeration or extrusion or compacting, in suitable granulation systems, of compositions of wettable powder type. The granules for dry-spreading are usually obtained by impregnation of a granular vehicle with a solution or an emulsion of the active materials.

The invention lastly relates to a treatment process intended to prevent fungal attacks on crops, characterized in that an effective and non-phytotoxic dose of a compound A chosen from iprodione, vinclozoline or procymidone, and a compound B which is cyprodinil, or of a composition according to the invention is applied to the aerial parts of the plants.

Among the fungal attacks which may be prevented by the process according to the invention, mention may be made of:

Botrytis cinerea (responsible for grey rot) in grape vines, market garden crops and peas, Venturia inaequalis (responsible for apple scab) in fruit trees producing seed-containing fruit, Monilia fructigena (responsible for moniliasis) in fruit trees producing kernel-containing fruit, phytopathogenic fungi of the genus Alternaria sp. (responsible for alternaria rot) in market garden crops, rapeseed, citrus fruits and Solanaceae, phytopathogenic fungi of the genus Ascochyta sp. (responsible for anthracnose) in peas, phytopathogenic fungi of the genus Penicillium sp. (responsible for moulds) in the preservation of fruits, Rhizoctonia solani (responsible for damping-off and necroses) in market garden crops and Solanaceae.

The combination or composition is advantageously used in such a way that the dose applied is such that the dose of the compound A is between about 200 and about 1000 g/ha, preferably between about 300 and about 600 g/ha, and that the dose of the compound B is between about 100 and about 500 g/ha, preferably between about 150 and about 400 g/ha. The dose applied is a fungicidally effective amount of the active ingredients A and B which is non-phytotoxic; preferably, a synergistic fungicidally effective amount of A and B is applied.

The example which follows is given as a non-limiting example of the advantageous properties of the compositions according to the invention.

EXAMPLE in vivo test of a composition comprising a mixture of iprodione and cyprodinil on Botrytis cinerea responsible for grey rot in cucumbers.

A commercial formulation of iprodione, which is a concentrated aqueous suspension, and a formulation, also commercially available, of cyprodinil, which is a dispersable granulate, are used.

Cucumber plants (Marketer variety) are cultivated in pots filled with peat/pozzolana. When these plants are 10 days old (cotyledon stage), they are treated by spraying with an aqueous suspension containing a mixture of the two active materials at the doses indicated in the table below.

After 24 hours, each plant is contaminated using an aqueous suspension of Botrytis cinerea spores (150,000 sp/cm$^3$) by depositing 5 drops onto the upper face of the 2 cotyledons.

After this contamination, the cucumber plants are placed in a moisture-saturated atmosphere for 7 days at 15° C.

The results are then read, by comparison with control contaminated cucumber plants which have not received the fungicidal treatment. In order to read the results, the number of drops of the contaminant suspension which gives rise to a so-called sporulant area, that is to say a spot of greyish and downy appearance, on the lower face of the cotyledons is determined.

The fungicidal efficacy, expressed as a percentage and indicated in the table below, is thus determined for each active material or mixture of active materials, at the dose indicated.

| | (doses in mg/l) | | | | | |
|---|---|---|---|---|---|---|
| | | Iprodione | | | | |
| Cyprodinil | 0 | 3 | 6 | 12 | 25 | 50 |
| 0 | 0 | 5.1 | 7.1 | 12.2 | 15.2 | 30.5 |
| 3 | 8.6 | | 22.3 | | | |
| 6 | 15.2 | 7.1 | 15.2 | 37.6 | | |
| 12 | 20.3 | | 30.5 | 28.9 | 46.2 | |
| 25 | 32.5 | | | 37.6 | 42.6 | 76.6 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A fungicidal combination comprising a synergistic fungicidally effective amount of a compound A which is iprodione, vinclozoline or procymidone and a compound B which is cyprodinil, the compound A/compound B weight ratio being between about 0.5 and about 5.

2. A combination according to claim 1, wherein the compound A/compound B weight ratio is between about 1 and about 3.

3. The combination according to claim 1, wherein compound A is iprodione.

4. The combination according to claim 2, wherein compound A is iprodione.

5. A fungicidal composition comprising a synergistic fungicidally effective amount of a combination of a compound A which is iprodione, vinclozoline or procymidone and a compound B which is cyprodinil, the compound A/compound B weight ratio being between about 0.5 and about 5, and at least one member selected from the group consisting of an agriculturally acceptable vehicle and an agriculturally acceptable surfactant.

6. A composition according to claim 5, wherein compound A and compound B together comprise from about 0.5% to about 95% of the composition.

7. A composition according to claim 5, wherein the compound A/compound B weight ratio is between about 1 and about 3.

8. The composition according to claim 5, wherein compound A is iprodione.

9. The composition according to claim 6, wherein compound A is iprodione.

10. The composition according to claim 7, wherein compound A is iprodione.

11. A method for preventing fungal disease in plants comprising applying a synergistic fungicidally effective amount of a compound A which is iprodione, vinclozoline or procymidone and a compound B which is cyprodinil to the aerial parts of said plants, the compound A/compound B weight ratio being between about 0.5 and about 5.

12. A method according to claim 11, wherein compound A is applied at a dose of between about 200 and about 1000 g/ha, and compound B is applied at a dose of between about 100 and about 500 g/ha.

13. A method according to claim 12, wherein compound A is applied at a dose of between about 300 and about 600 g/ha, and compound B is applied at a dose of between about 150 and about 140 g/ha.

14. A method according to claim 11, wherein compound A is iprodione.

15. A method for preventing fungal disease in plants comprising applying a synergistic fungicidally effective amount of a combination according to claim 1 to the aerial parts of said plants.

16. A method for preventing fungal disease in plants comprising applying a synergistic fungicidally effective amount of a composition according to claim 5 to the aerial parts of said plants.

* * * * *